United States Patent [19]

Bartek et al.

[11] 4,342,698

[45] Aug. 3, 1982

[54] OLEFIN OXIDATION PROCESS

[75] Inventors: Joseph P. Bartek, University Hts.; Robert K. Grasselli, Chagrin Falls; Rimvydas L. Cepulis, Willoughby Hills, all of Ohio

[73] Assignee: The Standard Oil Company, Cleveland, Ohio

[21] Appl. No.: 53,607

[22] Filed: Jun. 29, 1979

[51] Int. Cl.$^3$ ............... C07D 307/36; C07D 307/46; C07D 307/48; C07D 307/54

[52] U.S. Cl. .................... 549/505; 252/437; 252/439; 252/461; 252/462; 252/467; 252/469; 252/470; 252/472; 252/473; 252/474; 252/475; 252/476; 549/483; 549/484; 549/489; 549/506

[58] Field of Search ............. 260/346.11, 347.3, 347.8, 260/347.9

[56] References Cited

U.S. PATENT DOCUMENTS

| | | | |
|---|---|---|---|
| 2,900,396 | 8/1959 | Harrison | 260/346.11 |
| 3,238,225 | 3/1966 | Brill et al. | 260/346.11 |
| 3,328,315 | 6/1967 | Callahan et al. | 252/432 |
| 3,338,952 | 8/1967 | Callahan et al. | 260/465.3 |
| 3,894,055 | 7/1975 | Farha et al. | 260/346.11 |
| 3,912,763 | 10/1975 | Farha et al. | 260/346.11 |
| 3,928,389 | 12/1975 | Farha et al. | 260/346.11 |
| 4,039,476 | 8/1977 | Bertus et al. | 252/437 |
| 4,040,983 | 8/1977 | Innes et al. | 252/469 |
| 4,080,312 | 3/1978 | Farha et al. | 252/437 |

OTHER PUBLICATIONS

Shirai et al., Chemical Abstracts, vol. 75, (1971), 129649w.

Hasegawa et al., Chemical Abstracts, vol. 76, (1972), 99427y.

*Primary Examiner*—Richard Raymond
*Attorney, Agent, or Firm*—William A. Heidrich; Herbert D. Knudsen; Larry W. Evans

[57] ABSTRACT

Oxole compounds, e.g. furan, are produced by contacting alkenes and/or alkadienes with molecular oxygen in the presence of an antimony catalyst.

15 Claims, No Drawings

OLEFIN OXIDATION PROCESS

BACKGROUND OF THE INVENTION

This invention relates to a novel process for making oxoles. More particularly, this invention relates to the oxidation of alkenes and/or alkadienes to oxoles in the presence of an antimony oxide catalyst.

Oxole compounds react readily with oxygen under oxidative conditions to produce ring cleavage and the formation of polymers. Accordingly, the production of oxole compounds by the oxidation of hydrocarbons has generally been avoided. However, it has been discovered that oxole compounds can be produced by the oxidation of hydrocarbons in the presence of certain specific catalysts without substantial conversion of oxole compounds to undesirable products. In this regard, oxides of Co-Mo-P (U.S. Pat. No. 4,039,476), Fe-P (U.S. Pat. No. 3,928,389), V-P plus at least one of Fe, Co, Ni and Mo (U.S. Pat. No. 3,912,763), V-P-Mo (U.S. Pat. No. 4,080,312), Mo-Zn and at least one of Ni, Fe and Co (U.S. Pat. No. 3,894,055), Mo-Bi (U.S. Pat. No. 3,238,225) and Mn-Group VI metal (U.S. Pat. No. 2,900,396) have been used to catalyze this process. Each of these prior art catalysts appear to be disadvantageous for various different reasons. In particular, the use of these prior art catalysts result in low yields, low selectivity and low productivity. Thus, the search for additional catalysts suitable for this

SUMMARY OF THE INVENTION

It has now been discovered that alkenes and/or alkadienes can be oxidatized in the presence of antimony oxide catalysts to produce oxole compounds. In particular, it has been found that butene and/or butadiene can be catalytically oxidized to furan.

The instant invention provides a novel process for the production of an oxole comprising contacting at least one hydrocarbon selected from the group consisting of alkenes and alkadienes with oxygen in the presence of an antimony oxide catalyst. More specifically, the present invention provides a process for the catalytic oxidation of a hydrocarbon selected from the group consisting of alkenes and alkadienes in which the hydrocarbon and oxygen are contacted in the presence of a heterogenous catalyst of the formula:

$$A_aD_bSb_cP_dO_x$$

wherein
A is one or more elements selected from the group consisting of Fe, Co, Ni, U, Sn, Mn, La and the rare earth elements; and
D is one or more elements selected from the group consisting of Ag, Cu, Mo, V, W, Bi, Te, As, Se, Cr, Zr, Pb, Nb, Ti, Zn, Cd, alkaline earth elements and alkali metal elements;
and wherein
a is 0–10;
b is 0–10;
c is 1–10;
d is 0–20;
x is the number of oxygens required to satisfy the valence requirements of the other elements present.

In one embodiment, this invention provides a process for producing furan comprising contacting butadiene with air in the presence of a catalyst comprising an oxide complex of antimony and phosphorus.

DETAILED DESCRIPTION

The unsaturated oxole compounds produced by the process of the present invention comprise a five-membered oxygen-containing ring. Preferred oxole compounds have the formula:

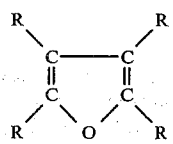

wherein each R is individually selected from the group consisting of hydrogen, alkyl radicals having from one to four carbon atoms, CHO, and COOH. Representative oxoles include furan, 2-methyl furan, 3-methyl furan, 2-5-diethylfuran, 2-n-hexylfuran, 2-isopropyl-3-methylfuran, 3-n-propylfuran, 3-methyl-4-n-butylfuran and furfural, furoic acid and the like. These oxoles are important chemical intermediates which are employed commercially on a large scale. They may also be used as solvents and resins.

Reactants

Suitable reactants for conversion to oxole compounds include alkenes and/or alkadienes, particularly the acyclic alkenes and acyclic alkadienes having from four to ten carbon atoms.

In a preferred embodiment, the oxole compounds are produced by the catalytic oxidation of alkadienes having the following structure:

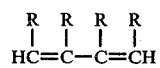

wherein each R is individually selected from the group consisting of hydrogen; alkyl radicals having from one to six carbon atoms; CHO; and COOH. More preferably, each R is individually selected from the group consisting of —H, —CH₃, and —CHO and most preferably R is hydrogen.

Examples of reactants useful in this invention include n-butene-1, butene-2, n-pentene-1, isopentene, hexene-1, heptene-2, oxtene-1, decene-1, 2-methylbutene-1, hexene-3, 2-ethylbutene-1, 2-methylpentene-3, 3-ethylhexene-2, butadiene-1,3, pentadiene-1,3, isoprene, hexadiene-1,3, decadiene-1,3, and the like, and mixtures thereof.

The alkenes, if present, are largely converted to the corresponding alkadienes. The alkadienes, in turn, are converted in significant quantities to the corresponding oxole compounds. If desired, the conversion of alkenes to oxole compounds can be conducted in two reaction zones in series. The first reaction zone can be operated under conditions favorable for the conversion of an alkene to an alkadiene, while the second reaction zone can be operated under the conditions favorable to the conversion of an alkadiene to an oxole compound. The catalyst of the present invention can be employed in both reaction zones, or another suitable dehydrogenation catalyst can be employed in the first reaction zone while the instant catalyst is utilized in the second reaction zone.

Any source of molecular oxygen can be employed in the instant process. Air is the preferred source. While the molar ratio of oxygen ($O_2$) to the alkene and/or alkadiene is not critical to the instant process, it is generally preferred to have an oxygen-hydrocarbon feed rate of from 0.1-4:1. More preferably, this feed rate is from 0.5-1.5:1.

Any material which is inert to the reactants, catalyst and products of this invention may also be included in the reaction system as a diluent. For example, water, recycled combustion gases, inert gases and nitrogen are preferred for reasons of convenience and economics.

It has also been discovered that it may be advantageous to add water in either its liquid form or vapor form to the reaction system. Thus, in one embodiment, 1-50 moles of water, preferably 5-30 moles of water, per mole hydrocarbon are added to the reaction system.

Finally, organic acids, such as maleic or acetic acid or their anhydrides, can be added to the instant process. These acids are useful in suppressing acid byproduct formation.

Process Conditions

In carrying out the process of this invention, a hydrocarbon feed comprising one or more alkenes and/or one or more alkadienes is contacted, under suitable reaction conditions, with a molecular oxygen containing gas in the presence of the catalysts disclosed below. This process can be accomplished in the batch mode or continuously in both fixed and fluid catalyst beds. The instant reaction can also take place in either the gas phase, liquid phase or a mixed gas/liquid phase.

Reaction temperatures are normally maintained between 150°-650° C., and more preferably between 300° and 550° C. The reaction pressures normally maintained at atmospheric pressure but may also be conducted at subatmosphere or superatmospheric pressure. The apparent contact time of the reactants with the catalyst may vary from about 0.01-20 seconds, more preferably 0.1-5 seconds, for the fixed-bed process. Longer contact times are normally used for fluid-bed processes. In general, lower reaction temperatures require longer contact times and higher reaction temperatures require shorter contact times. The hydrocarbon feed rate will generally be in the range of about 10-1,000 standard cubic ft. of hydrocarbon vapor per hour per cubic ft. of catalyst bed (ghsv) and preferably will be in the range of about 50-500 ghsv.

Catalyst

The catalyst employed in this process comprises an oxide or oxide complex. This catalyst can be described by the formula:

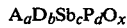

$A_a D_b Sb_c P_d O_x$ wherein
A is one or more elements selected from the group consisting of Fe, Co, Ni, U, Sn, Mn, La, and rare earth elements; and
D is one or more elements selected from the group consisting of Ag, Cu, Mo, V, W, Bi, Te, As, Se, Cr, Zr, Pb, Nb, Ti, Zn, Cd, alkaline earth elements and alkali metal elements; and
wherein
a is 0-10;
b is 0-10;
c is 1-10;
d is 0-20; and
x is the number of oxygens required to satisfy the valence requirements of the other elements present.

The catalyst can be any catalyst delineated by the general formula above with respect to components of the catalyst. Preferred catalysts are those wherein at least one of a and b are greater than 0. Furthermore, A is preferably one or more of Fe, U, Sn, Co and D is preferably one or more of W, Cu, Zr, Ag.

In one embodiment, the catalyst useful in the instant oxidation process contain phosphorus. These antimony-phosphorus oxide catalysts are particularly effective in converting alkenes and alkadienes to oxoles.

The exact chemical nature of this catalyst is not known. This catalyst may be a mixture of oxides, for example, or an oxide complex of all the contained elements. In any event, this type of catalyst is generally known in the art. For example, the disclosure in U.S. Pat. No. 3,338,952 shows catalyst compositions comprising iron antimony oxides and the disclosure in U.S. Pat. No. 3,328,315 discloses catalyst compositions comprising uranium antimony oxides. The catalyst of this invention can be made by techniques which are essentially the same as the techniques described in the above patents, which are herein incorporated by reference. Even though there are numerous preparations which may be utilized to give acceptable catalysts, some of the preferred methods of making the catalyst are described below.

The catalyst of this invention can be prepared from any mixture of compounds that can be calcined to give the desired oxide component. Preferably, the catalysts are prepared by coprecipitating decomposable salts such as nitrates, acetates, halides and/or oxides to form a catalyst precursor, and then calcining the precursor in the presence of oxygen. Other known catalyst preparation techniques, however, can be employed.

The catalytic activity embodied in the present invention is enhanced by heating the catalyst at elevated temperatures. Preferably, the catalyst is dried and heated at a temperature of 200° C.–1200° C., more preferably at about 300° C.–500° C., for from one-half to 24 hours. If the activity/selectivity relationship is not satisfactory the catalyst can be further heat treated at the temperature above about 300° C. but below a temperature deleterious to the catalyst.

The catalyst can be in the supported, unsupported or coated form. Preferred support materials are $Al_2O_3$, $SiO_2$, MgO, $Mg_2P_2O_7$, $BPO_4$, $AlPO_4$, $ZrP_2O_7$, $TiO_2$, $TiP_2O_7$ or any combination thereof. Any other known support material can be used which is stable under the reaction conditions to be encountered in the use of the catalyst. The support preferably comprises 5% to 95% by weight of the catalyst.

Recovery

The reaction product obtained upon completion of this reaction is composed primarily of oxole, unreacted reactants, alkenes including ethylene, propylene and butene, water, oxides of carbon, alkenylcycloolefins, crotonaldehyde, acetaldehyde and other oxygenated products. These reaction products can be subjected to suitable known separation techniques to yield the desired end product, mainly the oxole.

For example, the reactor gas can be condensed and the liquid products can then be separated by distillation. Unconverted alkenes/or alkadienes can be recovered and recycled to the reactor, as can other materials such as crotonaldehyde which are convertible to an oxole under the reaction conditions.

SPECIFIC EMBODIMENTS

In order to more thoroughly describe the present invention, the following working examples are presented. For the purposes of tabulating the results of these examples, the following definitions are used:

$$\text{Conversion} = \frac{\text{moles carbon in butadiene reacted}}{\text{moles carbon in butadiene fed}} \times 100$$

$$\text{Selectivity} = \frac{\text{moles carbon in furan produced}}{\text{moles carbon in reaction products}} \times 100$$

$$\text{Yield} = \frac{\text{moles carbon in furan produced}}{\text{moles carbon in butadiene fed}} \times 100$$

The results of the experiments are tabulated in Table I.

EXAMPLE 1

Butadiene was oxidized to furan in the presence of a catalyst comprising $SbO_x$ (20% $SiO_2$). This catalyst was prepared by mixing 102 grams of antimony trioxide with 190 cc of concentrated (70%) $HNO_3$ and 90 cc of $H_2O$. This mixture was boiled with reflux for three hours. After cooling, 22.6 grams of an amorphous colloidal silica (Cabosil MS-7) was added along with 100 cc $H_2O$. After stirring, the mixture was neutralized with concentrated $NH_3$ solution. A cream-colored paste, obtained after filtering and washing the mixture, was molded in a porcelain pan and dried at 110° C. overnight. The dried paste was then heated at 295° C. for three hours and 425° C. for three hours. The product was then calcined at 820° C. for 20 hours and the resultant catalyst was ground and screened to 20/35 mesh.

15 cc of the catalyst prepared above was placed in a fixed-bed stainless steel reactor. This reactor also contained a 10 cc preheater bed of inert particles which was at the top of the downflow reactor. Butadiene was fed as a vapor along with air and liquid water at the reaction conditions shown in Table I. The selectivity and yield to furan is also shown in Table I.

EXAMPLE 2

A catalyst comprising $NiSb_9O_x$ (20% $SiO_2$) was also used to oxidize butadiene to furan. This catalyst was prepared by mixing 65.5 grams of $Sb_2O_3$ in 400 milliliters of concentrated (70%) $HNO_3$. This mixture was refluxed for 4 hours and then 14.6 grams of $Ni(NO_3)_2 \cdot 6H_2O$ was added. The resultant mixture was stirred and heated for three hours and allowed to cool. Next, 17.4 grams of an amorphous colloidal $SiO_2$ powder (Cabosil MS-7) was added to form a light green slurry. This slurry was heated and stirred for three hours and then cooled and neutralized with concentrated $NH_3$ solution. This supernatant liquid was filtered and then washed with 1 liter of $H_2O$. After filtering again, the stiff cake is molded into holes in a Teflon ® plate and dried at 120° C. overnight to form four millimeter diameter pellets. The catalyst was heated for three hours at 295° C. and for three hours at 425° C. to remove the nitrates and then calcined for three hours at 800° C. to obtain a light gray-green solid.

The above catalyst was placed in the apparatus discussed in Example 1 under the conditions shown in Table I. The selectivity and yield to furan is also shown in Table I.

EXAMPLES 3–20

A variety of other catalysts were also used to oxidize butadiene to furan. The identity of these catalysts is disclosed in Table I. These catalysts were all prepared by techniques well known to those skilled in the art. The reactions were conducted with the apparatus disclosed in Example 1 under the conditions shown in Table I. The results are shown in Table I.

Although only a few embodiments of this invention have been specifically described above, it should be appreciated that many additions and modifications can be made without departing from the spirit and scope of the invention. These and all other modifications are intended to be included within the scope of this invention, which is to be limited only by the following claims:

TABLE I

OXIDATION OF BUTADIENE TO FURAN
Pressure: 1 Atmosphere

| Example | Catalyst | Temp. °C. | Butadiene Feed Rate (ghsv) | Contact Time (Sec.) | Butadiene Air/H$_2$O | Butadiene Conversion (%) | Furan Selectivity (%) | Furan Yield (%) |
|---|---|---|---|---|---|---|---|---|
| 1 | Sb$_2$O$_x$ (20% SiO$_2$) | 575 | 100 | 0.43 | 1/10/17 | 8.0 | 40.0 | 1.2 |
| 2 | NiSb$_9$O$_x$ (20% SiO$_2$) | 590 | 95 | 0.43 | 1/11/18 | 21.0 | 58.0 | 4.7 |
| 3 | FeSb$_9$O$_x$ (10% SiO$_2$) | 560 | 90 | 0.45 | 1/11/18 | 31.0 | 39.0 | 9.0 |
| 4 | FeSbO$_x$ (20% SiO$_2$) | 395 | 100 | 0.35 | 1/11/35 | 31.0 | 21.0 | 4.4 |
| 5 | CoSb$_9$O$_x$ (20% SiO$_2$) | 590 | 95 | 0.59 | 1/11/7 | 24.0 | 39.0 | 5.5 |
| 6 | CoSb$_4$O$_x$ (20% SiO$_2$) | 515 | 95 | 0.46 | 1/11/18 | 21.0 | 46.0 | 8.1 |
| 7 | USb$_{4.6}$O$_x$ (20% SiO$_2$) | 430 | 100 | 0.80 | 1/5/12 | 15.0 | 50.0 | 9.9 |
| 8 | " | 490 | 370 | 0.34 | 1/5/4 | 22.4 | 58.0 | 12.9 |
| 9 | " | 500 | 95 | 0.48 | 1/10/16 | 38.0 | 35.0 | 13.1 |
| 10 | SnSb$_4$O (20% SiO$_2$) | 530 | 95 | 0.47 | 1/11/17 | 21.0 | 44.0 | 8.2 |
| 11 | " | 560 | 95 | 0.44 | 1/10/17 | 26.0 | 38.0 | 10.7 |
| 12 | FeSbVO$_x$ (20% SiO$_2$) | 320 | 100 | 0.62 | 1/11/18 | 21.0 | 34.0 | 3.5 |
| 13 | SnCu$_{0.5}$W$_{0.5}$Sb$_4$O$_x$ (20% SiO$_2$) | 485 | 90 | 0.49 | 1/11/18 | 40.0 | 33.0 | 11.5 |
| 14 | SnCu$_{0.5}$W$_{0.5}$Sb$_4$O$_x$ (20% SiO$_2$) | 530 | 100 | 0.47 | 1/11/18 | 47.0 | 26.0 | 13.3 |
| 15 | SnCu$_{0.375}$Zr-W$_{0.015}$Sb$_3$O$_x$ | 455 | 90 | 0.51 | 1/11/18 | 25.0 | 40.0 | 6.9 |
| 16 | SnCu$_{0.375}$Zr-W$_{0.015}$Sb$_3$O$_x$ | 485 | 90 | 0.49 | 1/11/18 | 40.0 | 28.0 | 8.0 |
| 17 | SnAg$_{0.5}$Sb$_4$O$_x$ (20% SiO$_2$) | 485 | 90 | 0.48 | 1/11/18 | 19.0 | 35.0 | 4.5 |
| 18 | AgCaSb$_9$P$_{10}$O$_x$ | 540 | 90 | 0.45 | 1/11/18 | 13.0 | 40.0 | 5.1 |

TABLE I-continued

OXIDATION OF BUTADIENE TO FURAN
Pressure: 1 Atmosphere

| Example | Catalyst | Temp. °C. | Butadiene Feed Rate (ghsv) | Contact Time (Sec.) | Butadiene Air/H$_2$O | Butadiene Conversion (%) | Furan Selectivity (%) | Furan Yield (%) |
|---|---|---|---|---|---|---|---|---|
| 19 | K$_{0.1}$Ni$_{2.5}$Co$_{4.5}$Fe$_3$BiP$_{0.5}$Mo$_{10.8}$Sb$_{1.2}$-O$_x$ (20% SiO$_2$) | 400 | 100 | 0.50 | 1/5/27 | 28.5 | 42.0 | 11.9 |
| 20 | K$_{0.1}$Ni$_{2.5}$Co$_{4.5}$Fe$_3$BiP$_{0.5}$Mo$_{10.8}$Sb$_{1.2}$-O$_x$ (20% SiO$_2$) | 400 | 100 | 1.10 | 1/5/7 | 14.3 | 37.0 | 5.3 |
| 21 | K$_{0.1}$Ni$_{2.5}$Co$_{4.5}$Fe$_3$BiP$_{0.5}$Mo$_{10.8}$Sb$_{1.2}$-O$_x$ (20% SiO$_2$) | 370 | 250 | 0.40 | 1/5/10 | 32.0 | 32.0 | 10.0 |
| 22 | Sb$_8$ZrCuTe$_{0.5}$P$_{9.6}$-O$_x$ (20% SiO$_2$) | 430 | 100 | 0.70 | 1/5/15 | 32.8 | 37.0 | 12.3 |

We claim:

1. A process for producing an oxole comprising contacting at least one hydrocarbon selected from the group consisting of alkenes and alkadienes with oxygen in the presence of a heterogeneous catalyst represented by the formula:

$$A_a D_b Sb_c P_d O_x$$

wherein
A is one or more of the elements selected from the group consisting of Fe, Co, Ni, U, Mn, La, and rare earth elements; and
D is one or more elements selected from the group consisting of Ag, Cu, V, W, Bi, Te, As, Se, Cr, Zr, Pb, Nb, Ti, Zn, Cd, alkaline earth elements and alkali metal elements; and
wherein
a is greater than 0 to 10;
b is 0–10;
c is 1–10;
d is 0–20; and
x is the number of oxygens required to satisfy the valence requirements of the other elements present.

2. The process of claim 1 wherein A is at least one of Fe, U, and Co.

3. The process of claim 2 wherein A is at least one of U and Fe.

4. The process of claim 1 wherein D is at least one of W, Cu, Zr and Ag.

5. The process of claim 4 wherein D is at least one of W and Cu.

6. The process of claim 1 wherein b is greater than 0.

7. The process of claim 1 wherein said process is conducted in the vapor phase.

8. The process of claim 1 wherein said hydrocarbon contains from four to ten carbon atoms.

9. The process of claim 1 wherein said hydrocarbon is an alkadiene having the following structure:

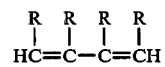

wherein each R is independently selected from the group consisting of (1) hydrogen; (2) alkyl radicals having from one to six carbon atoms; (3) CHO; and (4) COOH.

10. The process of claim 9 wherein R is selected from the group consisting of —H, —CH$_3$ and —CHO.

11. The process of claim 1 wherein water is added to the reaction system.

12. The process of claim 1 wherein at least one organic acid is added to the reaction system.

13. A process for the production of furan comprising contacting butadiene with air in the presence of the catalyst of claim 1.

14. A process for the production of furan comprising contacting butadiene with air in the presence of a catalyst comprising an oxide complex of antimony and phosphorus.

15. A process for producing an oxole comprising contacting at least one hydrocarbon selected from the group consisting of alkenes and alkadienes with oxygen in the presence of a heterogeneous catalyst represented by the formula:

$$A_a D_b Sb_c P_d O_x$$

wherein
A is one or more of the elements selected from the group consisting of Fe, Co, Ni, U, Sn, Mn, La, and rare earth elements; and
D is one or more elements selected from the group consisting of Ag, Cu, Mo, V, W, Bi, Te, As, Se, Cr, Zr, Pb, Nb, Ti, Zn, Cd, alkaline earth elements and alkali metal elements; and
wherein
a is greater than 0–10;
b is 0–10;
c is 1–10;
d is greater than 0 to 20; and
x is the number of oxygens required to satisfy the valence requirements of the other elements present.

* * * * *